US012629543B2

(12) United States Patent　　　(10) Patent No.: US 12,629,543 B2
Baba　　　(45) Date of Patent: May 19, 2026

(54) NEUTRON CAPTURE THERAPY APPARATUS

(71) Applicant: SUMITOMO HEAVY INDUSTRIES, LTD., Tokyo (JP)

(72) Inventor: Tatsuo Baba, Yokosuka (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 194 days.

(21) Appl. No.: 18/475,212

(22) Filed: Sep. 27, 2023

(65) Prior Publication Data

US 2024/0009485 A1　　Jan. 11, 2024

Related U.S. Application Data

(63) Continuation of application No. PCT/JP2022/014073, filed on Mar. 24, 2022.

(30) Foreign Application Priority Data

Mar. 30, 2021　(JP) ................................. 2021-057635

(51) Int. Cl.
A61N 5/10　　　(2006.01)
A61M 5/142　　(2006.01)

(52) U.S. Cl.
CPC ........... A61N 5/1048 (2013.01); A61M 5/142 (2013.01); A61M 2205/18 (2013.01); A61N 2005/1094 (2013.01)

(58) Field of Classification Search
CPC .......... A61N 5/1048; A61N 2005/1094; A61N 5/1077; A61N 2005/109; A61N 2005/1095; A61M 5/142; A61M 2205/18
See application file for complete search history.

(56) References Cited

U.S. PATENT DOCUMENTS

2013/0066135 A1* 3/2013 Rosa ......................... A61N 5/10
　　　　　　　　　　　　　　　　　　　　　　600/1
2021/0069528 A1　3/2021 Liu
2023/0372740 A1* 11/2023 Liu ...................... A61N 5/1079

FOREIGN PATENT DOCUMENTS

EP　　　　3 136 400 A1　8/2016
EP　　　　3136400 B1 * 11/2017 ........... A61N 5/1078
(Continued)

OTHER PUBLICATIONS

International Search Report of PCT/JP2022/014073, mailed on May 24, 2022.

(Continued)

*Primary Examiner* — Uzma Alam
*Assistant Examiner* — Mamadou Faye
(74) *Attorney, Agent, or Firm* — WTA IP Law P.C.

(57) ABSTRACT

A neutron capture therapy apparatus includes a neutron ray irradiation unit that irradiates an irradiation target with a neutron ray, a drug injection unit that injects a drug to the irradiation target, and a posture change unit that changes a posture of the irradiation target. The neutron ray irradiation unit performs first irradiation for irradiating the irradiation target with the neutron ray in a first incident direction, and performs second irradiation for irradiating the irradiation target with the neutron ray in a second incident direction different from the first incident direction, and the posture change unit is capable of changing the posture of the irradiation target between a time of the first irradiation and a time of the second irradiation.

15 Claims, 7 Drawing Sheets

(56)        References Cited

FOREIGN PATENT DOCUMENTS

| JP | 2008-22920 | A | 2/2008 | | |
| JP | 2015-231497 | A1 | 12/2015 | | |
| JP | 2017-042310 | A | 3/2017 | | |
| JP | 2019-177212 | A | 10/2019 | | |
| WO | WO-2015153946 | A1 * | 10/2015 | ............. | A61B 6/037 |
| WO | WO 2019/218915 | A1 | 11/2019 | | |

OTHER PUBLICATIONS

Office Action of the corresponding JP Application No. 2023-511133
Mailed on Feb. 3, 2026.

* cited by examiner

NEUTRON CAPTURE THERAPY APPARATUS

CROSS-REFERENCE TO RELATED APPLICATIONS

This is a bypass continuation of International PCT Application No. PCT/JP2022/014073, filed on Mar. 24, 2022, which claims priority to Japanese Patent Application No. 2021-057635, filed on Mar. 30, 2021, which are incorporated by reference herein in their entirety.

BACKGROUND

Technical Field

A certain embodiment of the present disclosure relates to a neutron capture therapy apparatus.

Description of Related Art

In recent years, there is a technique in which therapy is performed using a neutron ray. For example, boron neutron capture therapy (BNCT) using a boron compound is known as neutron capture therapy that irradiates a cancer cell with a neutron ray to kill the cancer cell. In the boron neutron capture therapy, boron that is taken into cancer cells in advance is irradiated with a neutron ray and the cancer cells are selectively destroyed using the scattering of heavy charged particles that is caused by the irradiation of boron with the neutron ray.

SUMMARY

A neutron capture therapy apparatus according to an aspect of the present disclosure includes: a neutron ray irradiation unit that irradiates an irradiation target with a neutron ray; a drug injection unit that injects a drug to the irradiation target; and a posture change unit that changes a posture of the irradiation target. The neutron ray irradiation unit performs first irradiation for irradiating the irradiation target with the neutron ray in a first incident direction, and performs second irradiation for irradiating the irradiation target with the neutron ray in a second incident direction different from the first incident direction; and the posture change unit is capable of changing the posture of the irradiation target between a time of the first irradiation and a time of the second irradiation.

A neutron capture therapy equipment according to another aspect of the present disclosure includes: a neutron capture therapy apparatus including a neutron ray irradiation unit that irradiates an irradiation target with a neutron ray, a drug injection unit that injects a drug to the irradiation target, and a posture change unit that changes a posture of the irradiation target; and an irradiation chamber in which the neutron ray irradiation unit, at least a part of the drug injection unit, and the posture change unit are disposed and the irradiation target is irradiated with the neutron ray. The neutron ray irradiation unit performs first irradiation for irradiating the irradiation target with the neutron ray in a first incident direction and performs second irradiation for irradiating the irradiation target with the neutron ray in a second incident direction different from the first incident direction, and the posture change unit is capable of changing the posture of the irradiation target between a time of the first irradiation and a time of the second irradiation.

DETAILED DESCRIPTION

Figure 1:
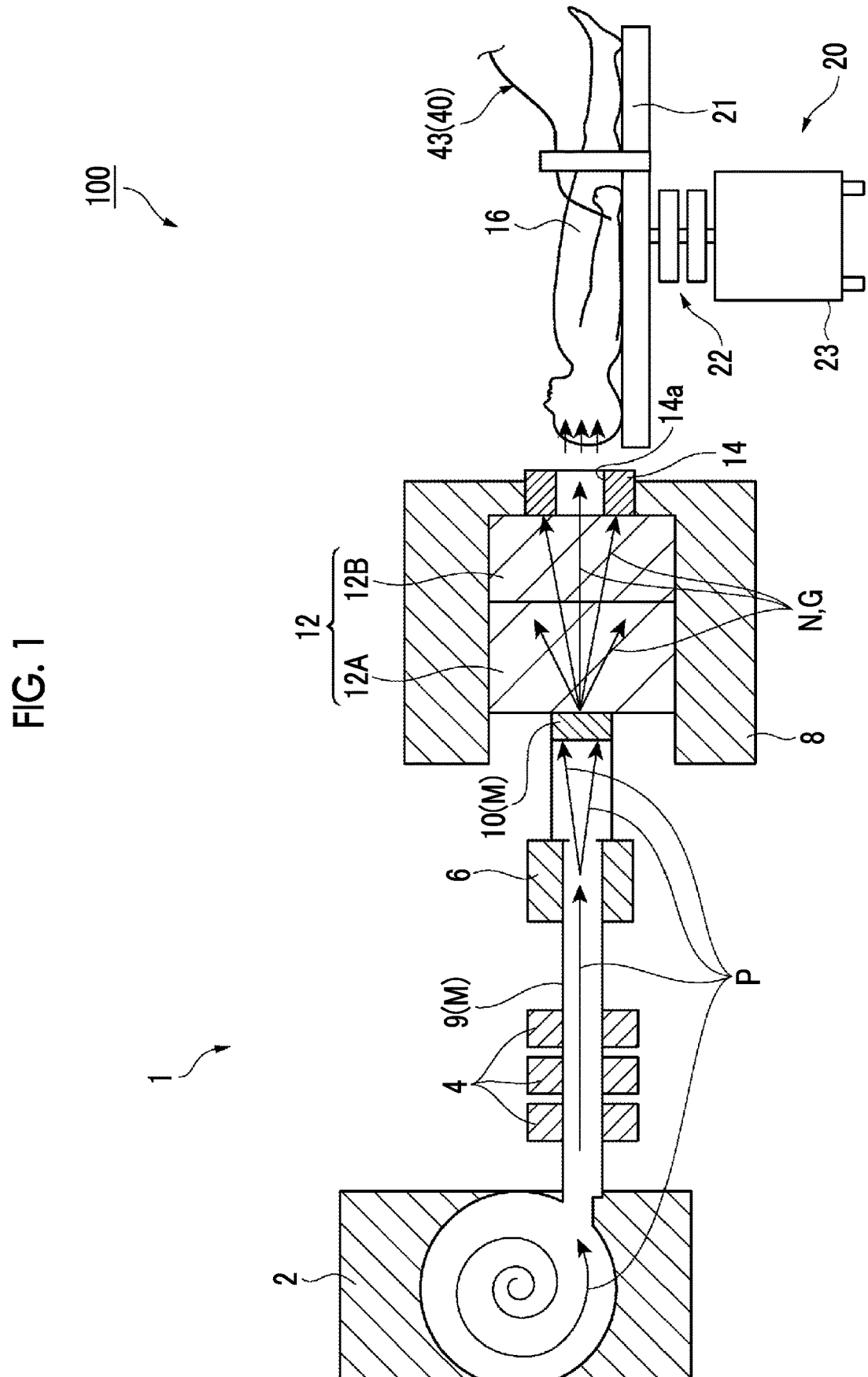
FIG. 1 is a schematic diagram showing a neutron capture therapy apparatus according to an embodiment.

Here, in a neutron capture therapy apparatus, a patient is fixed to a bed and is disposed in front of an irradiation port for a neutron ray. Accordingly, an affected part is irradiated with a neutron ray in one direction, so that the cancer cells of the affected part are destroyed. Here, the improvement of the uniformity of the radiation dose distribution of the neutron ray in the affected part is required in the neutron capture therapy.

Accordingly, it is desirable to provide a neutron capture therapy apparatus that can simply improve the uniformity of the radiation dose distribution of a neutron ray in an irradiation portion.

In the neutron capture therapy apparatus, the neutron ray irradiation unit performs the first irradiation for irradiating the irradiation target with the neutron ray in the first incident direction, and performs the second irradiation for irradiating the irradiation target with the neutron ray in the second incident direction different from the first incident direction. In this case, an irradiation portion in which the drug is taken can be irradiated with the neutron ray in directions different from each other, that is, the first incident direction and the second incident direction. For this reason, the irradiation portion can be irradiated with the neutron ray with high uniformity as compared to a case where the irradiation portion is irradiated with the neutron ray in one direction. Further, the posture change unit can change the posture of the irradiation target between the time of the first irradiation and the time of the second irradiation. In a case where the posture of the irradiation target is changed as described above, it is possible to simply irradiate the irradiation target with the neutron ray in different incident directions as compared to a case where a large-scale device is employed to drive the neutron ray irradiation unit. From the above description, the uniformity of the radiation dose distribution of the neutron ray in the irradiation portion can be simply improved.

The neutron capture therapy apparatus may further includes a pipe holding unit that holds a pipe of the drug injection unit. In a case where a placement part on which the irradiation target is placed is moved as the posture of the irradiation target is changed by the posture change unit, the pipe holding unit may be movable while maintaining a position relative to the placement part. In this case, the position of a portion of the pipe, which is positioned between the pipe holding unit and the irradiation target, relative to the irradiation target is substantially fixed even though the placement part is moved. For this reason, it is possible to suppress a reduction in flow rate, the closing of the flow channel, or the like that is caused by the pull-out of the pipe or the deformation of the pipe.

The drug injection unit may include a drug control unit that supplies the drug to the irradiation target via the pipe, and the pipe between the pipe holding unit and the drug control unit may be provided with a mechanism that absorbs a variation in length. The drug control unit may include a drug supply pump, and the drug supply pump may control an amount of the drug to be supplied per unit time. The drug control unit may be capable of detecting an abnormal state to give an alarm. In this case, even though the position of the pipe holding unit is moved, a variation in the length of the pipe caused by the movement of the position of the pipe holding unit is absorbed. Accordingly, the coming-off of the pipe from the irradiation target can be suppressed.

The drug injection unit may include a drug control unit that supplies the drug to the irradiation target via a pipe, and the drug control unit may be disposed in a protection region that is protected from radiation by having the radiation blocked. In this case, it is possible to suppress malfunction or the like that is caused by the exposure of the drug control unit to radiation.

The protection region may be formed by being separated from an irradiation chamber in which the irradiation target is irradiated with the neutron ray, by at least one of a shield wall and a shield door, and the drug control unit may be disposed in the protection region provided outside the irradiation chamber. In this case, it is possible to suppress malfunction or the like that is caused by the exposure of the drug control unit to radiation. Further, in a case where a drug bag is provided around the drug control unit, a worker can perform work in a state where the worker is protected from radiation when the worker replaces the drug bag or the like.

A pipe may extend from the drug control unit provided outside the irradiation chamber up to the irradiation target present in the irradiation chamber, and a guide part guiding the pipe may be provided in the irradiation chamber. The guide part may be provided with a plurality of slide holders that are slidable along the guide part, and the slide holders may hold respective portions of the pipe such that the pipe forms a waveform along the guide part. In this case, since the pipe is guided by the guide part, it is possible to suppress the entanglement of the pipe, and the like.

A shield casing blocking radiation may be disposed in an irradiation chamber in which the irradiation target is irradiated with the neutron ray, and the drug control unit may be disposed in the shield casing serving as the protection region. In this case, since the drug control unit can be disposed close to the irradiation target, the pipe can be shortened.

The shield casing may be provided on a moving body that moves together with the irradiation target. In this case, the pipe can be shortened.

The shield casing may be provided at a position separated from a moving body that moves together with the irradiation target. In this case, a structure can be made simple as compared to a case where the shield casing is provided on the moving body.

The posture change unit may be rotatable in a state where the irradiation target is placed. In this case, since the movement of the pipe caused by the rotational movement of the irradiation target is increased, an effect obtained from the use of the pipe holding unit is significant.

The neutron capture therapy equipment may further include a pipe holding unit that holds a pipe of the drug injection unit. In a case where a placement part on which the irradiation target is placed is moved as the posture of the irradiation target is changed by the posture change unit, the pipe holding unit may be movable while maintaining a position relative to the placement part.

The neutron capture therapy equipment may further include a protection region that is separated from the irradiation chamber by at least one of a shield wall and a shield door and is provided outside the irradiation chamber. The drug injection unit may include a drug control unit that supplies the drug to the irradiation target via a pipe, and the drug control unit may be disposed in the protection region.

According to these neutron capture therapy equipments, the same actions and effects as those of the above-mentioned neutron capture therapy apparatus can be obtained.

The neutron capture therapy equipment may further include a control unit that performs at least one of a control of a change in the posture of the irradiation target performed by the posture change unit and a control of the neutron ray irradiation unit, and a management chamber that is separated from the irradiation chamber by at least one of a shield wall and a shield door and is provided outside the irradiation chamber. The control unit is disposed in the management chamber. In this case, a change in the posture of the irradiation target performed by the posture change unit can be controlled by a remote operation from a place other than the irradiation chamber. In this case, since a worker does not have to directly change the posture of the irradiation target in the irradiation chamber, the exposure of the worker to radiation can be reduced.

A preferred embodiment of the present disclosure will be described in detail below with reference to the drawings.

Figure 2:
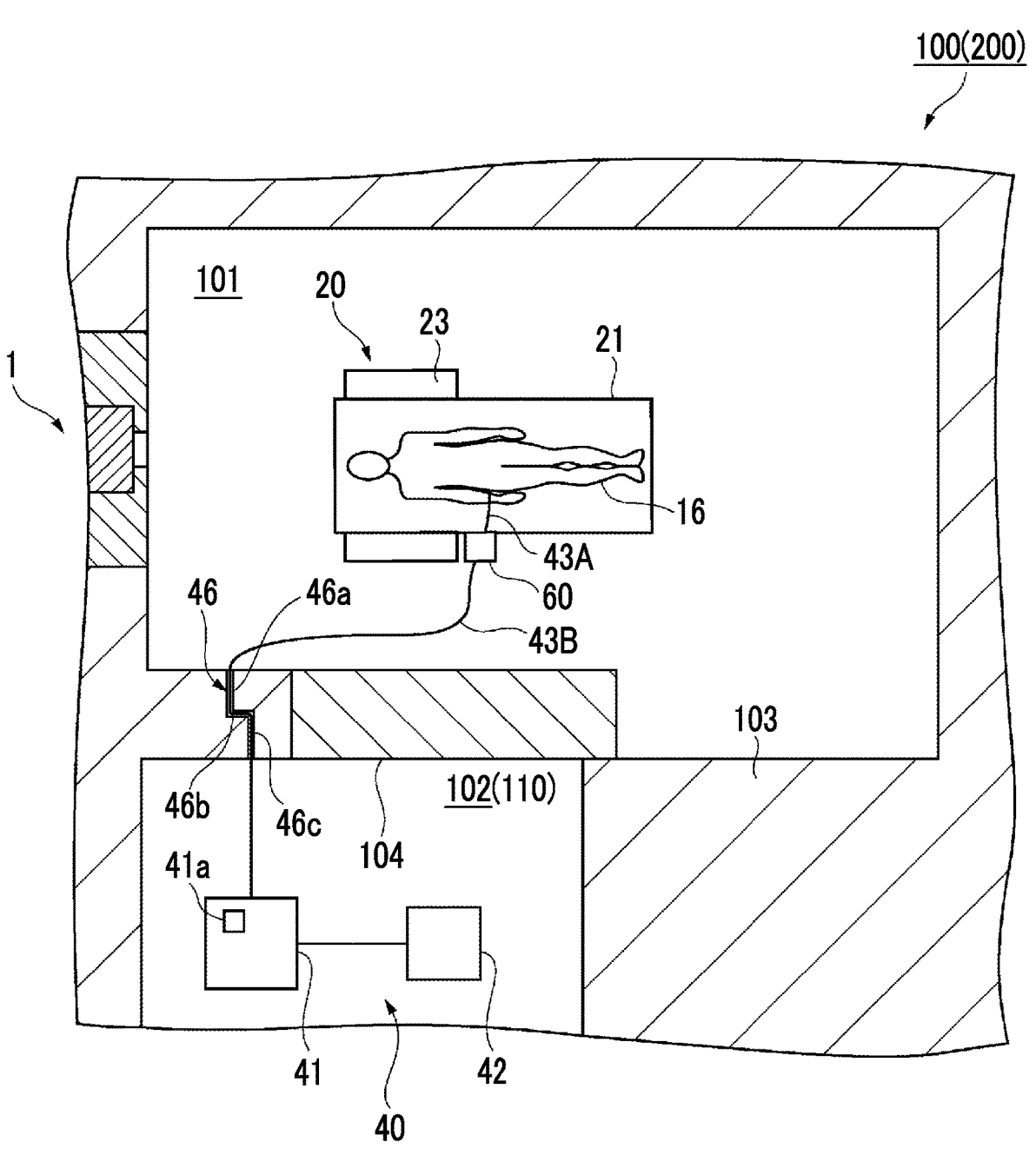
FIG. 2 is a schematic diagram showing the neutron capture therapy apparatus according to the embodiment and a neutron capture therapy equipment.

An overview of a neutron capture therapy apparatus according to an embodiment of the present disclosure will be described with reference to FIGS. 1 and 2. FIG. 1 is a schematic diagram showing the neutron capture therapy apparatus. FIG. 2 is a schematic plan view of the neutron capture therapy apparatus. The neutron capture therapy apparatus 100 (an example of a radiation therapy apparatus) shown in FIGS. 1 and 2 is an apparatus that performs cancer treatment using boron neutron capture therapy (BNCT). The neutron capture therapy apparatus 100 includes a neutron ray irradiation device 1 (neutron ray irradiation unit), a moving bed 20 (posture change unit), and a drug injection device 40 (drug injection unit).

First, the configuration of the neutron ray irradiation device 1 will be described with reference to FIG. 1. As shown in FIG. 1, the neutron ray irradiation device 1 irradiates a patient 16 (irradiation target) with a charged particle beam P (an example of radiation) including a neutron ray N and a gamma ray G. The neutron ray irradiation device 1 irradiates a tumor of the patient 16, to which a drug containing, for example, boron ($^{10}$B) is administered, with the neutron ray N.

The neutron ray irradiation device 1 includes an accelerator 2. The accelerator 2 accelerates charged particles, such as anions, and emits a charged particle beam P. The accelerator 2 is formed of, for example, a cyclotron. In the present embodiment, the charged particle beam P is a proton beam generated in a case where charges are stripped from anions. The accelerator 2 generates a charged particle beam P having, for example, a beam radius of 40 mm and 60 kW (=30 MeV×2 mA). The accelerator is not limited to the cyclotron, and may be a synchrotron, a synchrocyclotron, a linear accelerator, an electrostatic accelerator, or the like.

The charged particle beam P emitted from the accelerator 2 is sent to a neutron ray generating unit M provided in the neutron ray irradiation device 1. The neutron ray generating unit M includes a beam duct 9 and a target 10. The charged particle beam P emitted from the accelerator 2 passes through the beam duct 9 and travels toward the target 10 disposed at an end portion of the beam duct 9. A plurality of quadrupole electromagnets 4 and a scanning electromagnet 6 are provided along the beam duct 9. The plurality of quadrupole electromagnets 4 are to adjust a beam axis of the charged particle beam P using, for example, an electromagnet.

The scanning electromagnet 6 is to scan the charged particle beam P and to control irradiation of the target 10 with the charged particle beam P. The scanning electromagnet 6 controls an irradiation position of the charged particle beam P on the target 10.

The neutron ray irradiation device 1 irradiates the target 10 with the charged particle beam P to generate a neutron ray N and emits the neutron ray N to the patient 16 disposed on an examination table 17. The neutron ray irradiation device 1 includes the target 10, a shield member 8, a deceleration member 12, and a collimator 14.

The target 10 is irradiated with the charged particle beam P to generate radiation including the neutron ray N and the gamma ray G. The gamma ray G is generated with the generation of the neutron ray N. The target 10 is a solid-shaped member made of a material that generates a neutron ray and a gamma ray by being irradiated with a charged particle beam. Specifically, the target 10 is made of, for example, beryllium (Be), lithium (Li), tantalum (Ta), or tungsten (W), and has, for example, a disk-shaped solid shape having a diameter of 160 mm. The target 10 is not limited to the disk shape and may have another shape.

The deceleration member 12 is to decelerate the neutron ray N generated by the target 10 (reduces the energy of the neutron ray N). The deceleration member 12 may have a laminated structure including a layer 12A that mainly decelerates a fast neutron included in the neutron ray N and a layer 12B that mainly decelerates an epithermal neutron included in the neutron ray N.

The shield member 8 is to block the generated neutron ray N, the generated gamma ray G, and the like so that the generated neutron ray N, the generated gamma ray G, and the like are not emitted to the outside. The shield member 8 is provided to surround the deceleration member 12. An upper portion and a lower portion of the shield member 8 extend to an upstream side of the charged particle beam P more than the deceleration member 12.

The collimator 14 is to shape an irradiation field of the neutron ray N and includes an opening 14a through which the neutron ray N passes. The collimator 14 is, for example, a block-shaped member that includes the opening 14a at the center thereof.

The moving bed 20 is a device that maintains the posture of the patient 16 in a state where the patient 16 is placed at the irradiation position of the neutron ray N. Further, the moving bed 20 is movable in a horizontal direction in a state where the patient 16 is placed, and is rotatable. Specifically, the moving bed 20 includes a placement part 21 on which the patient 16 is to be placed, an adjustment mechanism 22 that adjusts the position and direction of the placement part 21, and a moving cart 23 that moves the entire moving bed 20. The placement part 21 is formed of a top board that can support the patient 16 in a state where the patient 16 is laid on an upper surface thereof. The adjustment mechanism 22 can move the placement part 21 in the horizontal direction. Further, the adjustment mechanism 22 can rotate the placement part 21 (see also FIGS. 3A, 3B, and 3C). The details of the operation of the moving bed 20 will be described later.

Next, the drug injection device 40 will be described with reference to FIG. 2. A neutron capture therapy equipment 200 in which the neutron capture therapy apparatus 100 is installed includes an irradiation chamber 101 in which the patient 16 is irradiated with the neutron ray N, and a preparation chamber 102 in which a preparation for treatment to be performed in the irradiation chamber 101 is made. Each chamber is covered with a shield wall 103 that blocks radiation. Further, the irradiation chamber 101 and the preparation chamber 102 are separated from each other by the shield wall 103 and a shield door 104. The preparation chamber 102 is a protection region 110 that is formed by being separated from the irradiation chamber 101 by the shield wall 103 and the shield door 104. The protection region 110 is a region that is protected from radiation by having the radiation blocked.

The drug injection device 40 includes a drug control unit 41, a drug bag 42, and a pipe 43. The drug control unit 41 is a unit that supplies a drug to the patient 16 via the pipe 43. The drug control unit 41 includes a drug supply pump 41a, and has a function to control the amount of drug to be supplied per unit time. The drug control unit 41 controls the drug supply pump 41a to inject the drug to the patient 16 from the drug bag 42 via the pipe 43. Further, the drug control unit 41 may have a function to detect various abnormal states and to give an alarm in addition to a function to control the amount of drug to be supplied.

The pipe 43 is a tube that includes a flow channel which is formed therein and through which the drug flows. One end of the pipe 43 is connected to the drug control unit 41, and an injection needle, such as a butterfly needle or an indwelling needle, is connected to the other end of the pipe 43. Then, the drug is supplied to the patient 16 via the injection needle. Here, the drug control unit 41 and the drug bag 42 are disposed in the preparation chamber 102, that is, the protection region 110 provided outside the irradiation chamber 101. Accordingly, the pipe 43, which connects the drug control unit 41 to the patient 16, passes through a communication portion 46 formed in the shield wall 103 and extends from the preparation chamber 102 up to the irradiation chamber 101. The communication portion 46 has the shape of a crank in a plan view, and includes a first portion 46a, a second portion 46b, and a third portion 46c.

Figure 3:
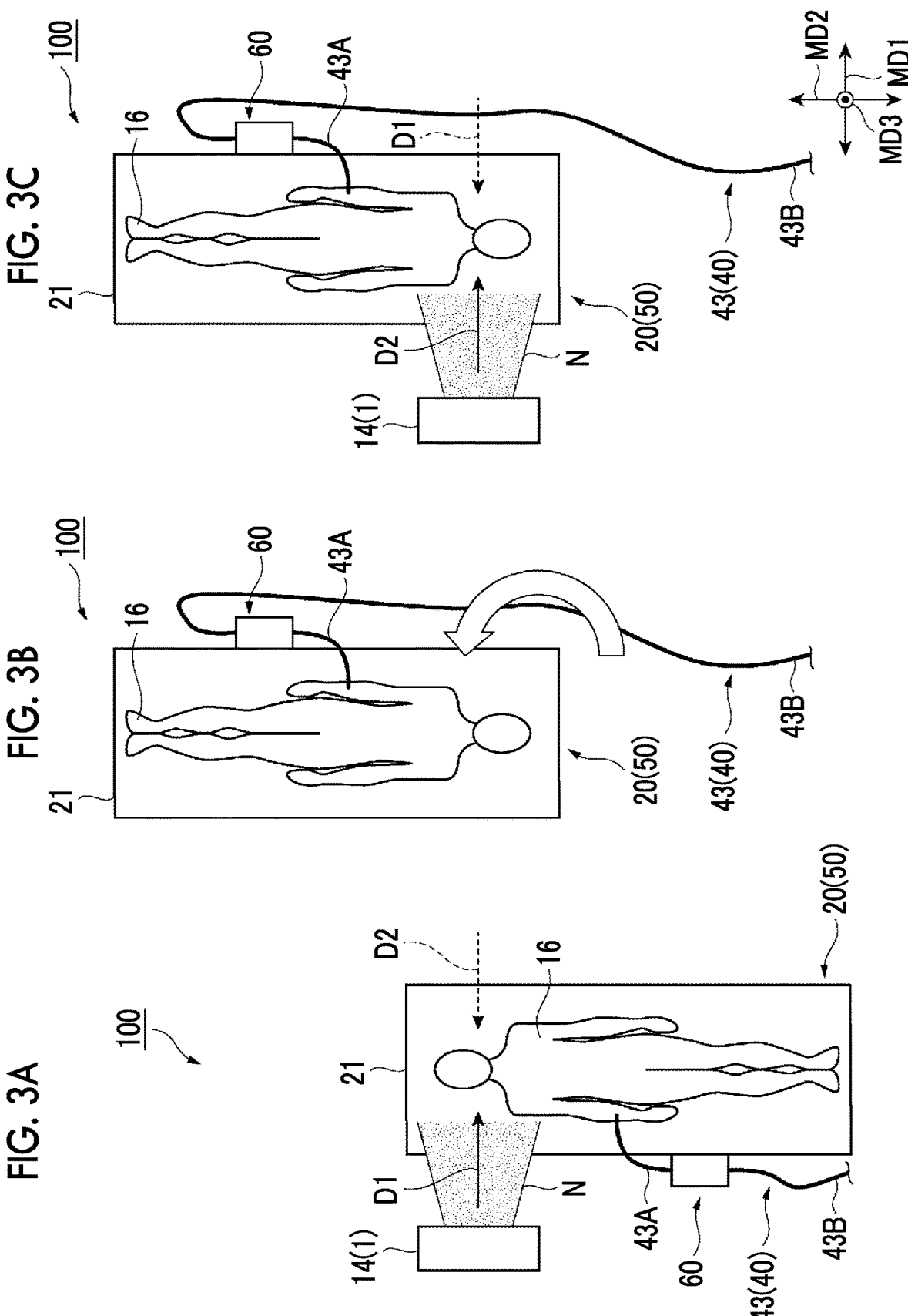
FIGS. 3A, 3B, and 3C are schematic diagrams showing a change in the posture of a patient during irradiation.

Here, the neutron capture therapy apparatus 100 according to the present embodiment irradiates the patient 16 with the neutron ray N relatively in a plurality of directions to improve the uniformity of the radiation dose distribution in an affected part. Accordingly, as shown in FIGS. 3A, 3B, and 3C, the neutron ray irradiation device 1 performs first irradiation (see FIG. 3A) for irradiating the patient 16 with the neutron ray N in a first incident direction D1, and performs second irradiation (see FIG. 3C) for irradiating the patient 16 with the neutron ray N in a second incident direction D2 relatively different from the first incident direction D1. The first incident direction D1 and the second incident direction D2 are directions in relative coordinates based on the patient 16. Since an irradiating direction in which the neutron ray irradiation device 1 emits the neutron ray N is constant in the present embodiment, the incident direction is switched via a change in the posture of the patient 16 with respect to the neutron ray irradiation device 1. The posture of the patient 16 mentioned here is the three-dimensional position and angle of the patient 16 with respect to the neutron ray irradiation device 1.

On the other hand, the moving bed 20 functions as a posture change unit 50 that can change the posture of the patient 16 between the time of the first irradiation and the time of the second irradiation. That is, the posture change unit 50 can adjust the position of the placement part 21 using the adjustment mechanism 22 (see FIG. 1) to change the posture of the patient 16 for each placement part 21. Further, since the adjustment mechanism 22 can rotate the placement part 21, the posture change unit 50 is rotatable in a state where the patient 16 is placed. As shown in FIG. 3A, the neutron ray irradiation device 1 performs the first irradiation to irradiate the patient 16 with the neutron ray N in the first incident direction D1. Next, as shown in FIG. 3B, the posture change unit 50 changes the posture of the patient 16 by rotating the placement part 21 to rotate the patient 16 by an angle of 180°. Then, as shown in FIG. 3C, the neutron ray irradiation device 1 performs the second irradiation to irradiate the patient 16 with the neutron ray N in the second incident direction D2. The posture change unit 50 not only may change the posture of the patient 16 via rotation, but also may translate the placement part 21 in any of translation directions MD1, MD2, and MD3 (see FIG. 3C) to change the posture of the patient 16.

In a case where the posture change unit 50 changes the posture of the patient 16 as described above, a portion of the pipe 43 pulled into the irradiation chamber 101 is also moved. Accordingly, in the present embodiment, as shown in FIGS. 3A, 3B, 3C, and 4, the neutron capture therapy apparatus 100 includes a pipe holding unit 60 that holds the pipe 43 of the drug injection device 40. In a case where the placement part 21 on which the patient 16 is placed is moved as the posture of the patient 16 is changed by the posture change unit 50, the pipe holding unit 60 is movable while maintaining a position relative to the placement part 21.

Figure 4:
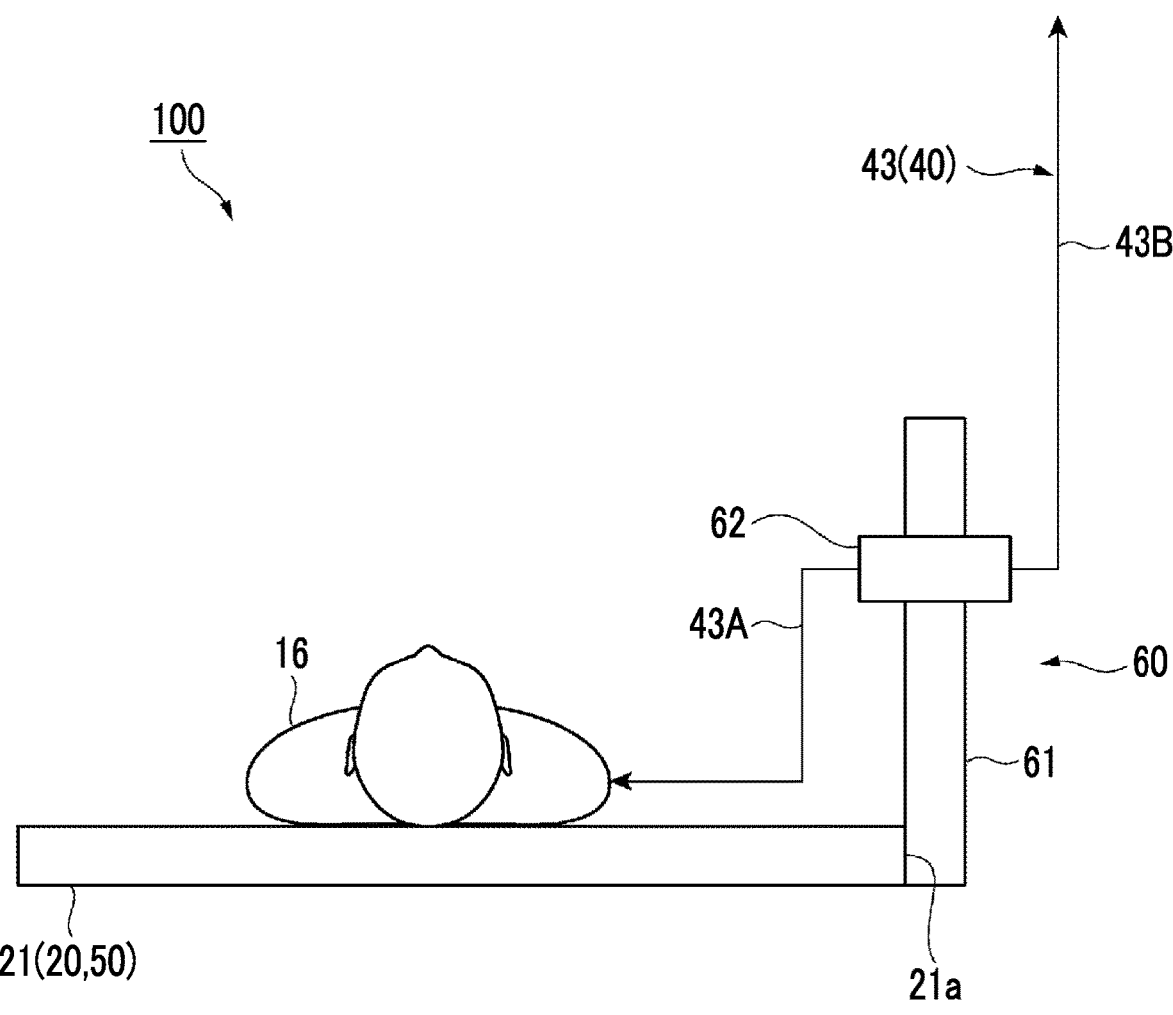
FIG. 4 is a schematic diagram schematically showing a pipe holding unit and a pipe.

Specifically, as shown in FIG. 4, the pipe holding unit 60 includes a jig 61 that is attached to the placement part 21, and a holder 62 that is attached to the jig 61 and holds the pipe 43. The jig 61 is provided at a portion of the placement part 21 close to a drug injection site (a site to which the injection needle is attached) of the patient 16. Here, since the drug is injected into an arm of the patient 16 (see FIGS. 3A, 3B, and 3C), the jig 61 is attached to a long side 21a of the placement part 21. The attachment position of the jig 61 to the placement part 21 may be changeable according to the drug injection site of the patient 16. The jig 61 extends upward from the placement part 21. The holder 62 is provided on the jig at a predetermined height position. The holder 62 is formed of a joint, a tube holder, or the like. In a case where the holder 62 is formed of a tube holder, it is preferable that the holder 62 holds the pipe 43 with a strength in a range where the flow channel of the pipe 43 is not crushed and a holding force that does not allow the holding position of the pipe 43 to be shifted during the movement of the placement part 21.

In a case where the holder 62 holds the pipe 43, the pipe 43 is separated into a stationary pipe portion 43A and a movable pipe portion 43B with the holder 62 as a boundary. The stationary pipe portion 43A extends from the holder 62 up to the drug injection site of the patient 16. The position of the holder 62 relative to the placement part 21 is fixed by the jig 61. Accordingly, the position of the stationary pipe portion 43A relative to the patient 16 is substantially fixed regardless of the movement of the placement part 21 as long as the patient 16 is not moved on the placement part 21. The movable pipe portion 43B extends from the holder 62 to the preparation chamber 102. The movable pipe portion 43B is moved in the irradiation chamber 101 as the placement part 21 is moved. For example, the state of the stationary pipe portion 43A shown in FIG. 3A and the state of the stationary pipe portion 43A shown in FIGS. 3B and 3C are the same as each other. On the other hand, the movable pipe portion 43B shown in FIGS. 3B and 3C is more stretched than the movable pipe portion 43B shown in FIG. 3A. The sufficient length of a portion of the movable pipe portion 43B disposed in the irradiation chamber 101 is ensured so that unnecessary tension does not act on the movable pipe portion 43B even though the placement part 21 is moved.

Figure 5:
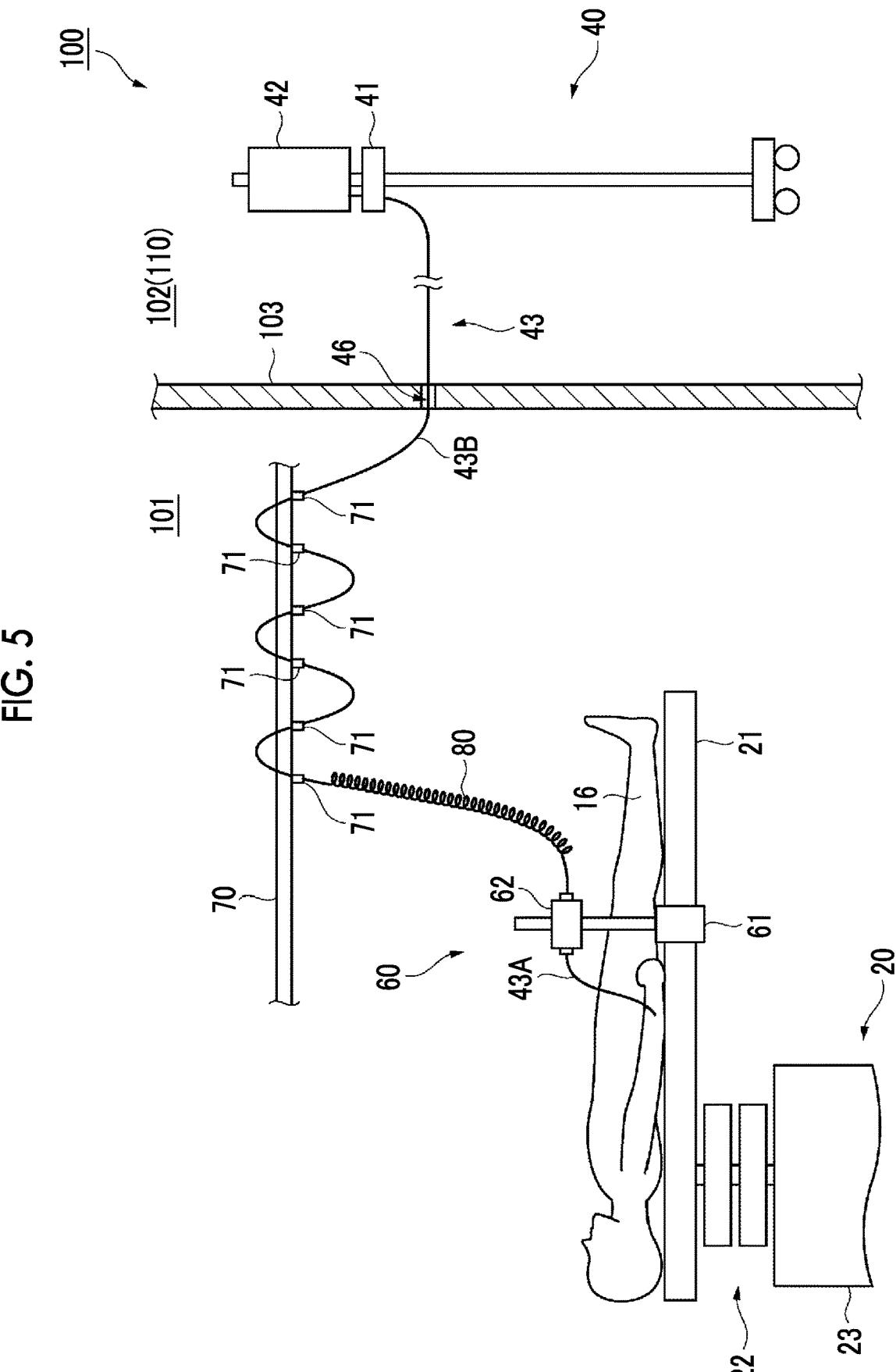
FIG. 5 is a schematic diagram showing an example of the configuration of the pipe.

Next, the movable pipe portion 43B of the pipe 43 will be described in more detail with reference to FIG. 5. As shown in FIG. 5, the movable pipe portion 43B extends from the holder 62 of the pipe holding unit 60 toward the communication portion 46 of the shield wall 103, passes through the communication portion 46, and extends up to the drug control unit 41.

Here, a guide part 70 guiding the movable pipe portion 43B is provided in the irradiation chamber 101. The guide part 70 extends from the shield wall 103 toward the position of the placement part 21 at a position higher than at least the placement part 21. The guide part 70 is provided with a plurality of slide holders 71 that are slidable along the guide part 70. The respective slide holders 71 hold the respective portions of the movable pipe portion 43B such that the movable pipe portion 43B forms a waveform along the guide part 70. As the holder 62 is moved away from the shield wall 103 in this case, the movable pipe portion 43B is moved away from the shield wall 103 together with the respective slide holders 71 such that the waveform is stretched along the guide part 70. On the other hand, as the holder 62 is moved close to the shield wall 103, the movable pipe portion 43B is moved close to the shield wall 103 together with the respective slide holders 71 such that the waveform is contracted along the guide part 70.

Further, the movable pipe portion 43B between the pipe holding unit 60 and the drug control unit 41 is provided with a variation absorption mechanism 80 that absorbs a variation in length. The variation absorption mechanism 80 is employed in a region between a portion of the movable pipe portion 43B, which is supported by the guide part 70, and the holder 62. Specifically, the variation absorption mechanism 80 is formed of a spiral tube (coiling tube) that is obtained in a case where the movable pipe portion 43B is wound in a spiral shape. As the holder 62 is moved away from the shield wall 103, the spiral structure of the movable pipe portion 43B is stretched at the portion of the variation absorption mechanism 80. As the holder 62 is moved close to the shield wall 103, the spiral structure of the movable pipe portion 43B returns to the original shape at the portion of the variation absorption mechanism 80. Such a variation absorption mechanism 80 can also suppress the twist of the movable pipe portion 43B. The movable pipe portion 43B between the pipe holding unit 60 and the drug control unit 41 may be provided with a rotary joint or the like as a twist suppression mechanism.

A work procedure of the neutron capture therapy apparatus 100 according to the present embodiment will be described. First, a worker places the patient 16 on the placement part 21 of the moving bed 20 in the preparation chamber 102, and performs work, such as aligning the patient 16 with the placement part 21 or fixing the position of the patient 16. Then, the worker attaches the injection needle, which is provided at the tip end of the pipe 43 of the drug injection device 40, to the patient 16 to inject the drug. Next, the moving cart 23 of the moving bed 20 is moved from the preparation chamber 102 to the irradiation chamber 101 in a state where the patient 16 is placed on the placement part 21. Then, the patient 16 is moved to a position where the first irradiation is performed. The injection needle may be attached to the patient 16 after the patient 16 is moved to the irradiation chamber 101.

The first irradiation is performed in a state where the shield door 104 is closed and the patient 16 is disposed at a first irradiation position (see FIG. 3A). The posture change unit 50 changes the posture of the patient 16 by rotationally moving the placement part 21 (see FIG. 3B). Then, the second irradiation is performed in a state where the patient 16 is disposed at a second irradiation position (see FIG. 3C). After the second irradiation ends, the patient 16 is evacuated from the irradiation chamber 101. Then, the worker detaches the injection needle of the pipe 43 from the patient 16 in the preparation chamber 102. Work for detaching the injection needle of the pipe 43 may be performed in the irradiation chamber 101.

Next, actions and effects of the neutron capture therapy apparatus 100 according to the present embodiment will be described.

From the viewpoint of the improvement of treatment efficiency, it is desirable to inject the drug to the patient using a drug control device or the like not only before the irradiation of the neutron ray but also during the irradiation of the neutron ray in the neutron capture therapy apparatus 100. Since radiation is generated in the irradiation chamber 101 during the irradiation, the drug control unit 41 is disposed outside the irradiation chamber 101 to avoid malfunction. Further, since the irradiation time of the neutron ray in the neutron capture therapy is long, it is necessary to replace the drug bag 42 during the irradiation. On the other hand, it is also necessary to dispose the drug bag 42 outside the irradiation chamber 101 to avoid the exposure of the worker to radiation. From the above description, a method of extending the pipe 43 from the drug control unit 41 and the drug bag 42 to inject the drug to the patient 16 present in the irradiation chamber 101 is employed.

Here, a treatment method of irradiating an object with a neutron ray in two or more incident directions (multiple-field irradiation) is employed to uniformize the radiation dose distribution of the neutron ray in an affected part. A structure for rotating an irradiation port for a neutron ray with a rotary gantry is also examined as a method of realizing the irradiation of the neutron ray in such multiple directions, but there are disadvantages in manufacturing cost and neutron shielding. On the other hand, since a method of rotating the placement part 21 to change the incident direction within a range in which the posture burden of the patient 16 is allowed is simpler, the method of rotating the placement part 21 is more effective in cost.

The concentration of a boron drug accumulated in the affected part of the patient 16 is reduced due to metabolism as time passes. Since the upper limit of the amount of drug, which can be administered to the patient 16 in one treatment, is determined, it is desirable to shorten the time from the completion of the first irradiation to the start of the second irradiation to reduce the amount of drug to be administered. Further, from the viewpoint of the improvement of treatment throughput as well, it is desirable that an interval time between the irradiations is short. Considering this, it is desirable to move the placement part 21 immediately after the completion of the first irradiation. However, since the irradiation chamber 101 is radioactivated still immediately after the irradiation, from the viewpoint of a reduction in the exposure of the worker to radiation, it is preferable to complete the work by remote operation so that the worker does not have to directly change the posture of the patient 16.

Therefore, in the neutron capture therapy apparatus 100 according to the present embodiment, the neutron ray irradiation device 1 performs the first irradiation for irradiating the patient 16 with the neutron ray N in the first incident direction D1, and performs the second irradiation for irradiating the patient 16 with the neutron ray N in the second incident direction D2 different from the first incident direction D1. In this case, an irradiation portion in which the drug is taken can be irradiated with the neutron ray N in directions different from each other, that is, the first incident direction D1 and the second incident direction D2. For this reason, the irradiation portion can be irradiated with the neutron ray N with high uniformity as compared to a case where the irradiation portion is irradiated with the neutron ray N in one direction. Further, the posture change unit 50 can change the posture of the patient 16 between the time of the first irradiation and the time of the second irradiation. In a case where the posture of the patient 16 is changed as described above, it is possible to simply irradiate the patient 16 with the neutron ray in different incident directions as compared to a case where a large-scale device, such as a gantry, is employed to drive the neutron ray irradiation device 1. From the above description, the uniformity of the radiation dose distribution of the neutron ray N in the irradiation portion can be simply improved.

Further, since the worker can change the incident direction without entering the irradiation chamber 101, the interval time is shortened. As a result, the second irradiation can be performed in a state where a reduction in the concentration of boron in the affected part is suppressed. Furthermore, since the worker can move the placement part 21 without entering the irradiation chamber 101, the exposure of the worker to radiation can be reduced. Moreover, since it is possible to cause the patient 16 to enter or leave the room remotely, it is not necessary to wait until the irradiation level in the irradiation chamber 101 is reduced. As a result, treatment throughput is improved. The neutron capture therapy apparatus 100 according to the present embodiment is effective in a case where irradiation is performed many times a day, and the like.

Here, in a case where the pipe 43 is pulled out due to pulling or the like or the flow channel is crushed due to twist during the movement of the placement part 21, there is a possibility that the flow rate of the drug, which can be injected, is reduced, or the like. However, from the viewpoint of a reduction in the exposure of the worker to radiation, it is also difficult to employ a method in which the worker enters the irradiation chamber 101 once to detach the injection needle.

Accordingly, the neutron capture therapy apparatus 100 may further include the pipe holding unit 60 that holds the pipe 43 of the drug injection device 40, and the pipe holding unit 60 may be movable while maintaining a position relative to the placement part 21 in a case where the placement part 21 on which the patient 16 is placed is moved as the posture of the patient 16 is changed by the posture change unit 50. In this case, the position of a portion of the pipe 43, which is positioned between the pipe holding unit 60 and the patient 16, relative to the patient 16 is substantially fixed even though the placement part 21 is moved. For this reason, it is possible to suppress a reduction in flow rate, the closing of the flow channel, or the like that is caused by the pull-out of the pipe 43 or the deformation of the pipe 43.

The drug injection device 40 may include the drug control unit 41 that supplies the drug to the patient 16 via the pipe 43, and the pipe 43 between the pipe holding unit 60 and the drug control unit 41 may be provided with the variation absorption mechanism 80 that absorbs a variation in length. In this case, even though the position of the pipe holding unit 60 is moved, a variation in the length of the pipe 43 caused by the movement of the position of the pipe holding unit 60 is absorbed. Accordingly, the coming-off of the pipe 43 from the patient 16 can be suppressed.

The drug injection device 40 may include the drug control unit 41 that supplies the drug to the patient 16 via the pipe 43, and the drug control unit 41 may be disposed in the protection region 110 that is protected from radiation by having the radiation blocked. In this case, it is possible to suppress malfunction or the like that is caused by the exposure of the drug control unit 41 to radiation.

The protection region 110 may be formed by being separated from the irradiation chamber 101 in which the patient 16 is irradiated with the neutron ray N by at least one of the shield wall 103 and the shield door 104, and the drug control unit 41 may be disposed in the protection region 110 provided outside the irradiation chamber 101. In this case, it is possible to suppress malfunction or the like that is caused by the exposure of the drug control unit to radiation. Further, in a case where the drug bag is provided around the drug control unit, the worker can perform work in a state where the worker is protected from radiation when the worker replaces the drug bag 42 or operates the drug control unit 41.

The pipe 43 may extend from the drug control unit 41 provided outside the irradiation chamber 101 up to the patient 16 present in the irradiation chamber 101, and the guide part 70 guiding the pipe 43 may be provided in the irradiation chamber 101. In this case, since the pipe 43 is guided by the guide part 70, it is possible to suppress the entanglement of the pipe 43, and the like.

The posture change unit 50 may be rotatable in a state where the patient 16 is placed thereon. In this case, since movement of the pipe 43 caused by the rotational movement of the patient 16 is increased, an effect obtained from the use of the pipe holding unit 60 is significant.

The neutron capture therapy equipment 200 according to the present embodiment includes: the neutron capture therapy apparatus 100 that includes the neutron ray irradiation device 1 irradiating an irradiation target with a neutron ray, the drug injection device 40 injecting the drug to the irradiation target, and the posture change unit 50 changing the posture of the irradiation target; and the irradiation chamber 101 in which the neutron ray irradiation device 1, at least a part of the drug injection device 40, and the posture change unit 50 are disposed and the irradiation target is irradiated with the neutron ray. The neutron ray irradiation device 1 performs the first irradiation for irradiating the irradiation target with the neutron ray in the first incident direction and performs the second irradiation for irradiating the irradiation target with the neutron ray in the second incident direction different from the first incident direction, and the posture change unit 50 can change the posture of the irradiation target between the time of the first irradiation and the time of the second irradiation.

The neutron capture therapy equipment 200 may further include the pipe holding unit 60 that holds the pipe 43 of the drug injection device 40, and the pipe holding unit 60 may be movable while maintaining a position relative to the placement part 21 in a case where the placement part 21 on which the irradiation target is placed is moved as the posture of the irradiation target is changed by the posture change unit 50.

The neutron capture therapy equipment 200 may include the protection region 110 that is separated from the irradiation chamber 101 by at least one of the shield wall 103 and the shield door 104 and is provided outside the irradiation chamber 101, the drug injection device 40 may include the drug control unit 41 that supplies the drug to the irradiation target via the pipe 43, and the drug control unit 41 may be disposed in the protection region 110.

According to these neutron capture therapy equipments 200, the same actions and effects as those of the above-mentioned neutron capture therapy apparatus 100 can be obtained.

The present disclosure is not limited to the above-mentioned embodiment.

Figure 6:
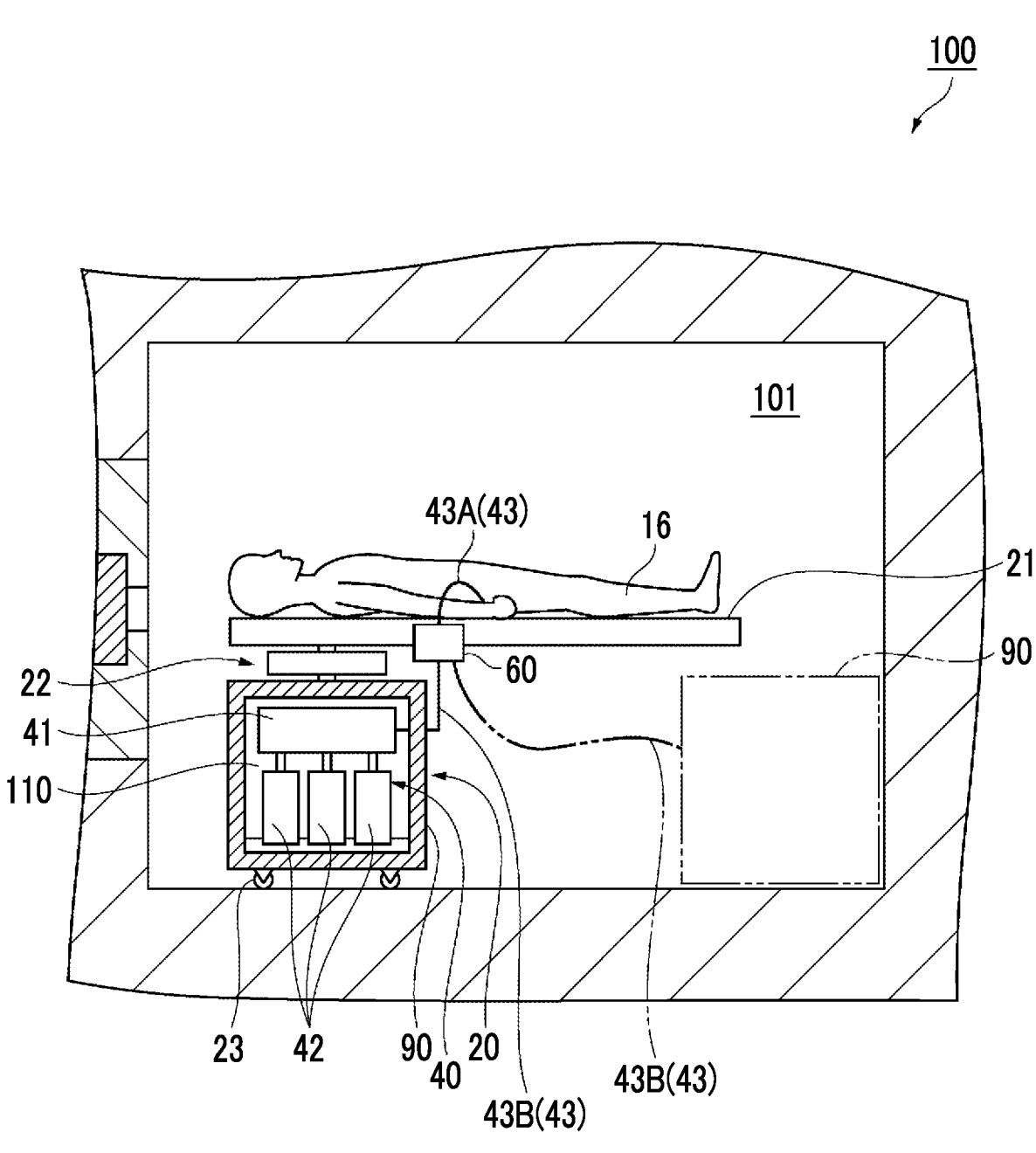
FIG. 6 is a schematic diagram showing a neutron capture therapy apparatus according to a modification example.

In the above-mentioned embodiment, the drug control unit 41 has been disposed in the protection region 110 provided outside the irradiation chamber 101. Instead of this, the drug control unit 41 may be disposed in a protection region 110 provided inside the irradiation chamber 101. For example, as shown in FIG. 6, a shield casing 90 blocking radiation is disposed in the irradiation chamber 101. In this case, an internal space of the shield casing 90 is the protection region 110 protected from radiation. Accordingly, the drug control unit 41 may be disposed in the shield casing 90 serving as the protection region 110. In the example shown in FIG. 6, the shield casing 90 is provided on a moving cart 23 serving as a moving body that moves together with a patient 16. A pipe 43 pulled from the drug control unit 41 provided in the shield casing 90 is held by the pipe holding unit 60 of the placement part 21, extends from the pipe holding unit 60, and is attached to the patient 16. In this case, a portion of the pipe 43 between the pipe holding unit 60 and the shield casing 90 is the movable pipe portion 43B. That is, since the placement part 21 is moved relative to the moving cart 23, the positions of the shield casing 90 and the pipe holding unit 60 are also changed in a case where the placement part 21 is moved. However, since the moving cart 23 and the shield casing 90 are disposed at a position close to the placement part 21, the movable pipe portion 43B can be shortened as compared to the example shown in FIG. 5. A plurality of (here, three) drug bags 42 are provided in the shield casing 90. The drug control unit 41 switches the drug bag 42 from which the drug is taken by controlling a three-way valve. Accordingly, even though the drug in the drug bag 42 runs out, a worker does not need to enter the irradiation chamber 101 and the drug bag 42 can be switched.

The shield casing 90 may be provided on the placement part 21 serving as a moving body that moves together with a patient 16. In this case, positions of the shield casing 90, the drug control unit 41, and the placement part 21 relative to each other are fixed. Accordingly, even though the pipe holding unit 60 is not provided, the positions of the pipe 43 and the patient 16 relative to each other are substantially fixed.

Further, as shown in FIG. 6 by an imaginary line, the shield casing 90 may be provided at a position separated from the moving bed 20 that is a moving body moving together with the patient 16.

As described above, the shield casing 90 blocking radiation is disposed in the irradiation chamber 101 in which the patient 16 is irradiated with the neutron ray N and the drug control unit 41 may be disposed in the shield casing 90 serving as the protection region 110. In this case, since the drug control unit 41 can be disposed close to the patient 16, the pipe 43 can be shortened.

The shield casing 90 may be provided on a moving body that moves together with the patient 16. In this case, the pipe 43 can be shortened.

The shield casing 90 may be provided at a position separated from a moving body that moves together with the patient 16. In this case, a structure can be made simple as compared to a case where the shield casing 90 is provided on the moving body.

As long as the posture change unit 50 (moving bed 20) can change the posture of the irradiation target, any unit may be used as the posture change unit 50 and the mechanism thereof is not limited to the above-mentioned embodiment. Further, the posture change unit 50 may include a control device (not shown) that controls the adjustment mechanism 22 to adjust the position of the placement part 21.

Figure 7:
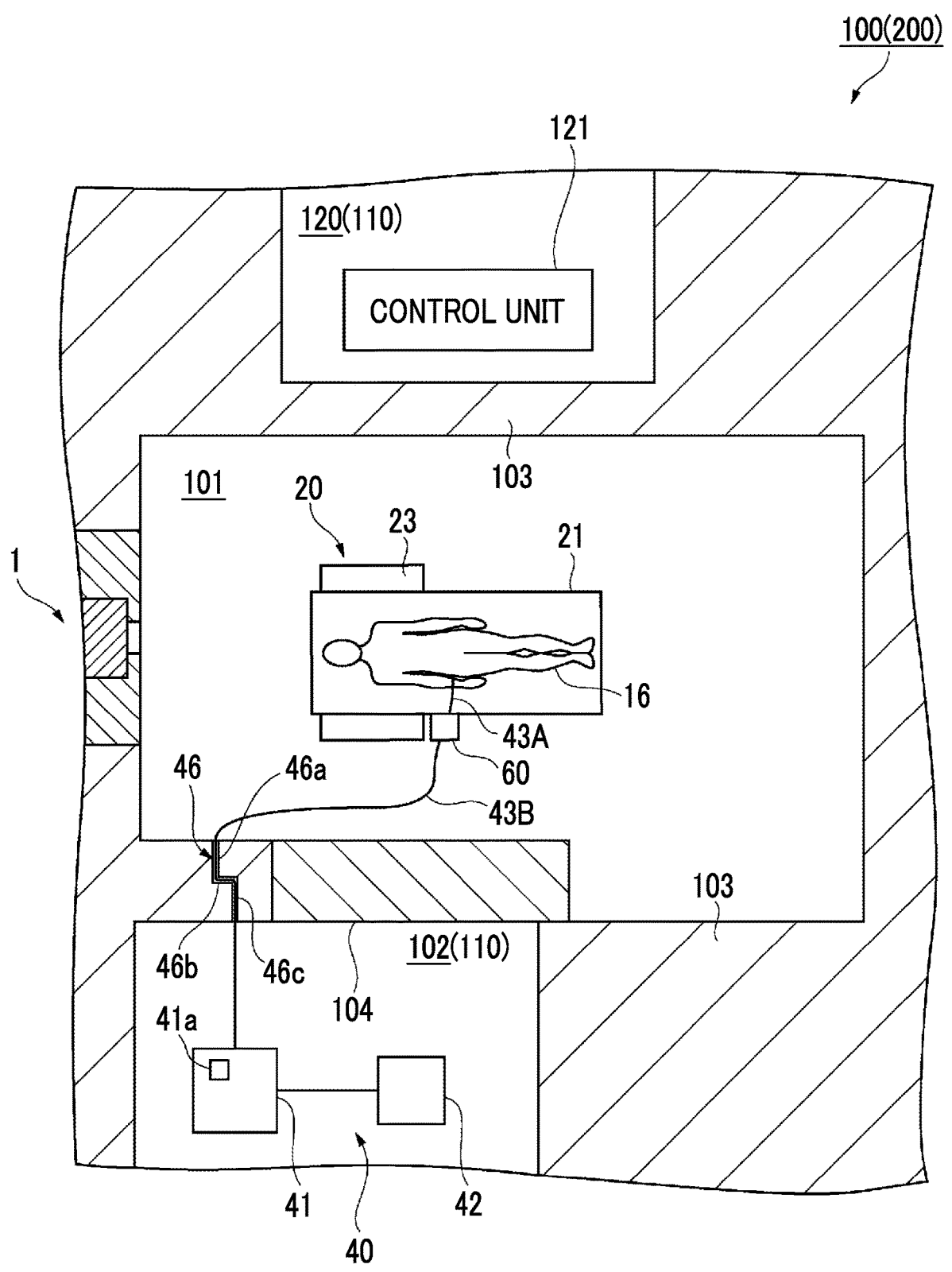
FIG. 7 is a schematic diagram showing a neutron capture therapy equipment according to a modification example.

As shown in FIG. 7, a neutron capture therapy equipment 200 is a modification example of the neutron capture therapy equipment shown in FIG. 2, and is different from the neutron capture therapy equipment shown in FIG. 2 in that the neutron capture therapy equipment 200 includes a management chamber 120. The neutron capture therapy equipment 200 includes a control unit 121 that performs at least one of the control of a change in the posture of the irradiation target performed by the posture change unit 50 and the control of the neutron ray irradiation device 1, and a management chamber 120 that is separated from the irradiation chamber 101 by at least one of the shield wall 103 and the shield door 104 and is provided outside the irradiation chamber 101; and the control unit 121 is disposed in the management chamber 120. In the present embodiment, the management chamber 120 is disposed at a position adjacent to the irradiation chamber 101 on a side opposite to the preparation chamber 102. Since the management chamber 120 is separated from the irradiation chamber 101 by the shield wall 103, the management chamber 120 is formed as a protection region 110.

The control unit 121 is connected to the neutron ray irradiation device 1 and the posture change unit 50, and controls the neutron ray irradiation device 1 and the posture change unit 50. The control unit 121 controls the posture change unit 50 such that the moving cart 23 of the moving bed 20 is moved from the preparation chamber 102 to the irradiation chamber 101 in a state where a patient 16 is placed on the placement part 21. Then, the control unit 121 moves the patient 16 to a position where the first irradiation is performed. The control unit 121 performs the first irradiation in a state where the shield door 104 is closed and the patient 16 is disposed at the first irradiation position (see FIG. 3A). The control unit 121 changes the posture of the patient 16 by controlling the posture change unit 50 to rotationally move the placement part 21 (see FIG. 3B). Then, the control unit 121 performs the second irradiation in a state where the patient 16 is disposed at the second irradiation position (see FIG. 3C).

According to the neutron capture therapy equipment 200, a change in the posture of the patient 16 performed by the posture change unit can be controlled by a remote operation from a place other than the irradiation chamber 101. In this case, since a worker does not have to directly change the posture of the irradiation target in the irradiation chamber 101, the exposure of the worker to radiation can be reduced. Further, the worker can control the neutron ray irradiation device 1 with a remote operation from the outside of the irradiation chamber 101.

It should be understood that the invention is not limited to the above-described embodiment, but may be modified into various forms on the basis of the spirit of the invention. Additionally, the modifications are included in the scope of the invention.

What is claimed is:

1. A neutron capture therapy apparatus comprising:
a neutron ray irradiator configured to irradiate an irradiation target with a neutron ray;
a drug injector configured to inject a drug to the irradiation target;
a moving bed configured to change a posture of the irradiation target; and
a pipe holder configured to hold a pipe of the drug injector,
wherein the neutron ray irradiator performs first irradiation for irradiating the irradiation target with the neutron ray in a first incident direction, and performs second irradiation for irradiating the irradiation target with the neutron ray in a second incident direction different from the first incident direction,
the moving bed is capable of changing the posture of the irradiation target between a time of the first irradiation and a time of the second irradiation, and
in a case where a placement part on which the irradiation target is placed is moved as the posture of the irradiation target is changed by the moving bed, the pipe holder is movable while maintaining a position relative to the placement part.

2. The neutron capture therapy apparatus according to claim 1,
wherein the drug injector includes a drug controller configured to supply the drug to the irradiation target via the pipe, and
the pipe between the pipe holder and the drug controller is provided with a mechanism that absorbs a variation in length.

3. The neutron capture therapy apparatus according to claim 2,
wherein the drug controller includes a drug supply pump, and the drug supply pump controls an amount of the drug to be supplied per unit time.

4. The neutron capture therapy apparatus according to claim 2,
wherein the drug injector is capable of detecting an abnormal state to give an alarm.

5. The neutron capture therapy apparatus according to claim 1,
wherein the drug injector includes a drug controller configured to supply the drug to the irradiation target via a pipe, and
the drug controller is disposed in a protection region that is protected from radiation by having the radiation blocked.

6. The neutron capture therapy apparatus according to claim 5,
wherein the protection region is formed by being separated from an irradiation chamber in which the irradiation target is irradiated with the neutron ray, by at least one of a shield wall and a shield door, and
the drug controller is disposed in the protection region provided outside the irradiation chamber.

7. The neutron capture therapy apparatus according to claim 6,
wherein the pipe extends from the drug controller provided outside the irradiation chamber up to the irradiation target present in the irradiation chamber, and
a guide part guiding the pipe is provided in the irradiation chamber.

8. The neutron capture therapy apparatus according to claim 7, wherein the guide part is provided with a plurality of slide holders that are slidable along the guide part, and the slide holders hold respective portions of the pipe such that the pipe forms a waveform along the guide part.

9. The neutron capture therapy apparatus according to claim 5, wherein a shield casing blocking radiation is disposed in an irradiation chamber in which the irradiation target is irradiated with the neutron ray, and the drug controller is disposed in the shield casing serving as the protection region.

10. The neutron capture therapy apparatus according to claim 9, wherein the shield casing is provided on a moving body that moves together with the irradiation target.

11. The neutron capture therapy apparatus according to claim 9, wherein the shield casing is provided at a position separated from a moving body that moves together with the irradiation target.

12. The neutron capture therapy apparatus according to claim 1, wherein the moving bed is rotatable in a state where the irradiation target is placed.

13. A neutron capture therapy equipment comprising:

a neutron capture therapy apparatus including a neutron ray irradiator configured to irradiate an irradiation target with a neutron ray, a drug injector configured to inject a drug to the irradiation target, a moving bed configured to change a posture of the irradiation target, and a pipe holder configured to hold a pipe of the drug injector; and an irradiation chamber in which the neutron ray irradiator, at least a part of the drug injector, and the moving bed are disposed and the irradiation target is irradiated with the neutron ray, wherein the neutron ray irradiator performs first irradiation for irradiating the irradiation target with the neutron ray in a first incident direction, and performs second irradiation for irradiating the irradiation target with the neutron ray in a second incident direction different from the first incident direction, the moving bed is capable of changing the posture of the irradiation target between a time of the first irradiation and a time of the second irradiation, and in a case where a placement part on which the irradiation target is placed is moved as the posture of the irradiation target is changed by the moving bed, the pipe holder is movable while maintaining a position relative to the placement part.

14. The neutron capture therapy equipment according to claim 13, further comprising:

a protection region that is separated from the irradiation chamber by at least one of a shield wall and a shield door and is provided outside the irradiation chamber, wherein the drug injector includes a drug controller configured to supply the drug to the irradiation target via the pipe, and the drug controller is disposed in the protection region.

15. The neutron capture therapy equipment according to claim 13, further comprising:

a controller configured to perform at least one of a control of a change in the posture of the irradiation target performed by the moving bed and a control of the neutron ray irradiator; and a management chamber that is separated from the irradiation chamber by at least one of a shield wall and a shield door and is provided outside the irradiation chamber, wherein the controller is disposed in the management chamber.

* * * * *